(12) United States Patent
Vertesy et al.

(10) Patent No.: US 7,253,206 B2
(45) Date of Patent: Aug. 7, 2007

(54) PHENALENONE DERIVATIVES, PROCESSES FOR PREPARATION AND USE THEREOF

(75) Inventors: Laszlo Vertesy, Eppstein-Vockenhausen (DE); Michael Kurz, Hofheim (DE); Ziyu Li, Offenbach (DE); Luigi Toti, Hochheim (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 539 days.

(21) Appl. No.: 10/367,545

(22) Filed: Feb. 14, 2003

(65) Prior Publication Data

US 2004/0014807 A1 Jan. 22, 2004

Related U.S. Application Data

(60) Provisional application No. 60/366,744, filed on Mar. 22, 2002.

(30) Foreign Application Priority Data

Feb. 18, 2002 (DE) ............................... 102 06 849

(51) Int. Cl.
- *A01N 31/35* (2006.01)
- *C12P 17/00* (2006.01)
- *C12P 7/00* (2006.01)
- *C12P 7/22* (2006.01)
- *C12P 1/04* (2006.01)

(52) U.S. Cl. ...................... 514/454; 514/453; 435/117; 435/132; 435/156; 435/170

(58) Field of Classification Search ................ 435/117, 435/132, 156, 170; 514/453, 454, 732
See application file for complete search history.

(56) References Cited

U.S. PATENT DOCUMENTS 5,932,613 A * 8/1999 Jiang et al. .................. 514/510

FOREIGN PATENT DOCUMENTS

| JP | 60199849 | 10/1985 |
|---|---|---|
| JP | 03124791 | 5/1991 |
| WO | WO99/60992 | 12/1999 |
| WO | WO 00/45165 | 8/2000 |

OTHER PUBLICATIONS

"Cecil Textbook of Medicine" Goldman and Bennett, Eds. 21st edition. (2000) (W.B. Saunders Company: Philadelphia, PA), pp. 1060-1074.*
"Taber's Cyclopedic Medical Dictionary" Clayton, Ed. 15th edition. (1985) (F.A. Davis Company: Philadelphia, PA) p. 1162.*
Levine, R. "Carbonyl modified proteins in cellular regulation, aging, and disease" Free Radical Biol. Med. (2002) 32(9): 790-796.*
Rice-Evans, et al. "Current status of antioxidant therapy" Free Radical Biol. Med. (1993) 15(1): 77-96.*
Matter et al. "Recent advance in the design of matrix metalloprotease inhibitos" Current Opinion in Drug Discovery & Develop.(2004) 7(4): 513-535.*
Barton, D H R et al., The Constitutions of Atrovenetin and of Some Related Herqueinone Derivatives, Tetrahedron; 1959; vol. 6; pp. 48-62.
Frost David A et al., Naturally Occurring Compounds related to Phenalenone. Part VI. Synthesis of Atrovenetin (8,9-Dihydro-3,4,5,6-tetrahydroxy-1,8,8,9-tetra-methytphenateno[1,2-b]furan-7-one) and RElated Compounds, Journal of Chemical Society, Perkin Trans.1; 1973; vol. 20; pp. 2388-2396.
Hart Roger et al., Etylenediaminetetraacetic Acid and Related Chelating Agents, Ullman's Encyclopedia of Industrial Chemistry; 5th Edition; Years 1985-1995; vol. A 10; pp. 95-100.
Ishikawa Yukihiro et al., Atrovenetin as a Potent Antioxidant Compound from Penicillium Species, Journal Am. Oil Chem. Society, 1991; vol. 68; pp. 666-668.
Muller J et al., Methoden der Mikrobiologie, Franck'sche Verlagsgesellschaft; 1964; pp. 189-192.

(Continued)

*Primary Examiner*—Leon B. Lankford, Jr.
*Assistant Examiner*—Susan Hanley
(74) *Attorney, Agent, or Firm*—Balaram Gupta

(57) ABSTRACT

The present invention provides novel phenalenone derivatives of formula (I) which are formed by the microorganism *Penicillium herquei* Bainer & Sartory, DSM 14142, during fermentation. A process for their preparation, their use as pharmaceutical compositions, and their use for the treatment or prophylaxis of bacterial infections, mycoses, oncoses and rheumatic diseases are also disclosed and claimed

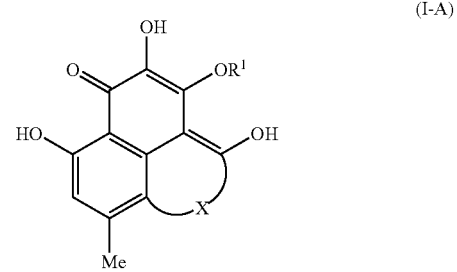

(I-A)

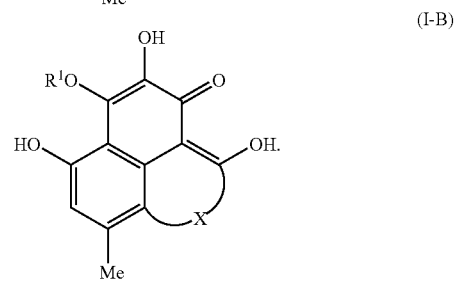

(I-B)

15 Claims, No Drawings

OTHER PUBLICATIONS

Narasimhachari N et al., Herqueichrysin, a New Phenalenone Antibiotic from Penicillium Herqueli, Journal of Antibiotics; 1972; vol. 25; pp. 155-162.

Ostrakhovitch Elana A et al., Oxidative Stress in Rheumatoid Arthritis Leukocytes: Suppression by Rutin and Other Antioxidants and Chelators, Biochemical Pharmacology; 2001; vol. 62; pp. 743-746.

Simpson Thomas J. Carbon-13 Nuclear Magnetic Resonance Structural and Biosynthetic Studies on Deoxyherqueinone and Herqueichrysin, Phenalenone Metabolites of Penicillium herquei, Journal of the Chemical Society; Perkin Trans. 1; 1979; pp. 1233-1238.

Suga Takayuki et al., 13C NMR Signal Assignments of Herqueinone and Its Phenalenone Derivatives, Bulletin of Chemical Society Jpn; 1983; vol. 56; pp. 3661-3666.

Ayer William A et al., Metabolites produced by the Scleroderris canker fungus, Gremmeniella abietina. Part 4.1 Biosynthetic studies, Canadian Journal of Chemistry, vol. 65, 1987, pp. 760-764.

Buchi George et al., Total Syntheses of Atrovenetin and Scleroderodione, Journal of Organic Chemistry, vol. 51, 1986, pp. 4813-4818.

Frost D A et al., Metabolitic Products of P. Herquei, Tetrahedron Letters. No. 46, 1972, pp. 4729-4732.

E.S. Waight, Mass Spectrometry of some Phenalene Derivatives and Related Compounds, Some Newer Phys. Methods Struct. Chem., Proc. Symp., 1967, Meeting Date 1966, 67-74; Bonnet R., Ed., Publisher: United Trade Press Ltd., London, England (1966, pp. 67-74).

I. C. Paul et al., Fungal Metabolites. Part III. The Structure of Atrovenetin: X-Ray Analysis of Altroveneth Orange Trimethyl Ether Ferrichloride, J. Chem. Soc. (1965, pp. 1097-1112).

* cited by examiner

PHENALENONE DERIVATIVES, PROCESSES FOR PREPARATION AND USE THEREOF

This application claims the benefit of German priority document number 10206849.6, filed Feb. 18, 2002, and U.S. Provisional Application No. 60/366,744, filed Mar. 22, 2002.

BACKGROUND OF THE INVENTION

1. Field of the Invention

The present invention relates to phenalenone derivatives which are formed by the microorganism *Penicillium herquei* Bainer & Sartory, DSM 14142 during fermentation, processes for their preparation, their use as pharmaceutical compositions, and their use for the treatment or prophylaxis of bacterial infections, mycoses, oncoses and rheumatic diseases.

2. Description of the Art

Cancer is a disease of humans and animals which usually takes a fatal course and which is caused by the uncontrolled growth of endogenous cells. Cancer is the term for the formation of malignant growths (malignomas), of neoplasms (tumors and carcinomas) or for the malignant degeneration and maturation disorder of white blood cells (leukemia, blood cancer). Cancer or tumor cells are formed by conversion of endogenous cells. The malignancy of the cancer cell is expressed in the autonomy of growth, that is, its ability to grow is uninhibited in an infiltrating manner and without classification in the constructional plan of the organs and with tissue destruction. A certain sign of malignancy is the formation of tumor-remote deposits (metastases) after hematogenic or lymphogenic spread of tumor cells. Cancer is among the most frequent causes of death of man and therefore there is a great need for methods and means for the cure or treatment of malignant degenerations.

Possible therapy for malignant tumors includes, in addition to radical surgical removal of the tumor where possible, radiological therapy using X-rays, α-, β-, γ-rays, immunotherapy and chemotherapy. Immunotherapy can at present only be used to a restricted extent. The chemotherapy of tumors is understood as meaning the administration of cell toxins (cytostatics) for the treatment of tumors and of remaining tumor cells after local surgical treatment or irradiation. These substances specifically intervene in certain processes of cell division, so that tissue having a high proportion of dividing cells, such as the rapidly growing tumor tissue, react more sensitively. Alkylating compounds, such as, for example, cyclophosphamide, (The Merck Index, 12th ed. page 463), antimetabolites, such as methotrexate (The Merck Index, 12th ed. page 1025), alkaloids, such as vincristine (The Merck Index, 12th ed. page 1704) and antibiotics, such as daunomycin (The Merck Index, 12th ed. page 479) and adriamycin (The Merck Index, 12th ed. pages 581-582) are used. However, all of these agents feature certain disadvantages on account of severe side effects, so that the death of the afflicted person is only delayed, but not averted. Moreover, in degenerated (cancer) cells, when resistance to the agents used occurs, the present medicaments then no longer act cytostatically, but exhibit toxic side effects. Moreover, it has been shown that a combined or sequential administration of cytostatics augments the activity of an individual cytostatic (monotherapy) and it is thereby possible that significant side effects are not additive in polychemotherapy. For all these reasons, novel chemotherapeutics are urgently needed and therefore sought worldwide.

Natural substances having a phenalenone parent structure have already been described. Phenalene is a fused, partially aromatic ring system, which decomposes in air. Phenalenone is its oxidation product having a carbonyl group in the 1-position.

The patent application WO 99/60992 generically describes phenalenones, which in all positions apart from C1 can be substituted by hydrogen or $C_1$-$C_4$-alkyl, preferably methyl, or $C_1$-$C_4$-alkoxy, preferably methoxy, for use as hair colorants.

Japanese patent application JP 60199849 describes the phenalenone derivative 2,7,8,9-tetrahydroxy-4-methoxy-5-methylphenalen-1-one, which is active as a phosphodiesterase (PDE) inhibitor and can be used for the treatment of arteriosclerosis, bronchial asthma, diabetes and cancers.

D. A. Frost & G. A. Morrison; (J. Chem. Soc., Perkin Trans. 1, 20, 2388-2396, 1973) describe the isolation of norxanthoherquein (2,3,4,7,8,9-hexahydroxy-5-methyl-phenalen-1-one) from *Penicillium herquei* Bainer & Sartory.

D. H. R. Barton et al. (Tetrahedron, 6, 48, 1959) describe the isolation of atrovenetin from *Penicillium atrovenetum* and from *Penicillium herquei* Bainer & Sartory. Atroventin is described as an antioxidant by Y. Ishikawa et al. (J. Am. Oil Chem. Soc. 68, 666-668, 1991), and as a cytostatic having antineoplastic activity in WO 00/45165.

N. Narasimhachari and L. C. Vining (J. Antibiotics, 25, 155, 1972) and J. Simpson (Chem. Soc. Perkin Trans. 1, 1979, 1233-1238) describe tautomeric forms of the compound desoxyherqueinone (2-O-methylatrovenetin), which are isolable from *Penicillium herquei* and exhibit antibiotic activity against gram-positive organisms.

The object of the present invention is to provide alternative phenalenone derivatives which can be used in tumor therapy.

SUMMARY OF THE INVENTION

Specifically, the invention relates to a compound of the formula (I-A), or

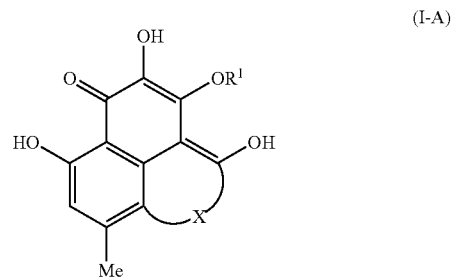

of formula (I-B),

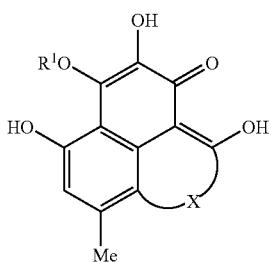

(I-B)

wherein:
X is a group of formula (I-C), or

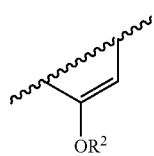

(I-C)

of formula (I-D),

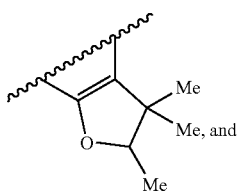

(I-D)

$R^1$ and, if present, $R^2$ simultaneously are H, $C_1$-$C_6$-alkyl, $C_2$-$C_6$-alkenyl or $C_2$-$C_6$-alkynyl, wherein said $C_1$-$C_6$-alkyl, $C_2$-$C_6$-alkenyl or $C_2$-$C_6$-alkynyl substituents are optionally mono- or disubstituted by —OH, =O, —O—$C_1$-$C_6$-alkyl, —O—$C_2$-$C_6$-alkenyl, —$C_6$-$C_{10}$-aryl, —NH—$C_1$-$C_6$-alkyl, —NH—$C_2$-$C_6$-alkenyl, —NH$_2$, or halogen, wherein said —O—$C_1$-$C_6$-alkyl, —O—$C_2$-$C_6$-alkenyl, —$C_6$-$C_{10}$-aryl, —NH—$C_1$-$C_6$-alkyl, and —NH—$C_2$-$C_6$-alkenyl substituents are optionally substituted by —CN, —NH—C(=O)—($C_1$-$C_6$)-alkyl or =NOH, or a stereoisomeric form of the compound of formula (I-A) or (I-B), or mixtures of the stereoisomeric forms thereof in any ratio, or a pharmaceutically acceptable salt thereof, and with the proviso that when $R^1$ is H, X is the group of formula (I-C).

$R^1$ and $R^2$ are preferably H or $C_1$-$C_6$-alkyl.

DETAILED DESCRIPTION OF THE INVENTION $C_1$-$C_6$-alkyl is a linear or branched alkyl having 1 to 6 C atoms, preferably having 1 to 4 C atoms, e.g. methyl, ethyl, i-propyl, tert-butyl and hexyl.

$C_2$-$C_6$-alkenyl is a linear or branched alkenyl having 2 to 6 C atoms, which is mono-, di- or triunsaturated, e.g. allyl, crotyl, 1-propenyl, penta-1,3-dienyl and pentenyl.

$C_2$-$C_6$-alkynyl is a linear or branched alkynyl having 2 to 6 C atoms, which is mono- or di-unsaturated, e.g. propynyl, butynyl and pentynyl.

$C_6$-$C_{10}$-aryl is an aryl group having 6 to 10 C atoms, e.g. phenyl, benzyl or 1- or 2-naphthyl, which can also be optionally substituted, for example by halogen, such as chlorine, bromine, or fluorine, by alkyl having 1-4 C atoms, preferably methyl, by hydroxyl, by alkoxy having 1-4 C atoms, in particular methoxy, or by trifluoromethyl.

The substituent —NH—C(O)—($C_1$-$C_6$-alkyl) is defined as an amide wherein $C_1$-$C_6$-alkyl is a linear or branched alkyl having 1 to 6 C atoms, preferably having 1 to 4 C atoms, e.g. methyl, ethyl, i-propyl, tert-butyl and hexyl.

As used herein, 'R' and 'S' are used as commonly used in organic chemistry to denote specific configuration of a chiral center. The term 'R' (rectus) refers to that configuration of a chiral center with a clockwise relationship of group priorities (highest to second lowest) when viewed along the bond toward the lowest priority group. The term 'S' (sinister) refers to that configuration of a chiral center with a counterclockwise relationship of group priorities (highest to second lowest) when viewed along the bond toward the lowest priority group. The priority of groups is based upon sequence rules wherein prioritization is first based on atomic number (in order of decreasing atomic number). A listing and discussion of priorities is contained in *Stereochemistry of Organic Compounds*, Ernest L. Eliel, Samuel H. Wilen and Lewis N. Mander, editors, Wiley-Interscience, John Wiley & Sons, Inc., New York, 1994.

In addition to the (R)-(S) system, the older D-L system may also be used herein to denote absolute configuration, especially with reference to amino acids. In this system a Fischer projection formula is oriented so that the number 1 carbon of the main chain is at the top. The prefix 'D' is used to represent the absolute configuration of the isomer in which the functional (determing) group is on the right side of the carbon at the chiral center and 'L', that of the isomer in which it is on the left.

As used herein, 'stereoisomer' or 'stereoisomeric form' is a general term used for all isomers of individual molecules that differ only in the orientation of their atoms in space. The term stereoisomer includes mirror image isomers (enantiomers), mixtures of mirror image-isomers (racemates, racemic mixtures), geometric (cis/trans or E/Z) isomers, and isomers of compounds with more than one chiral center that are not mirror images of one another (diastereoisomers). Chiral centers, if not stated otherwise, are present in the R configuration or in the S configuration. The invention relates both to the optically pure compounds and to stereoisomeric mixtures, such as enantiomeric mixtures and diastereomeric mixtures, in any ratio.

As used herein, "tautomer" or "tautomerism" refers to the coexistence of two (or more) compounds that differ from each other only in the position of one (or more) mobile atoms and in electron distribution, for example, keto-enol tautomers or tautomerism.

As used herein, "halogen" or "hal" means fluorine, chlorine, bromine and iodine.

As used herein, 'treat' or 'treating' means any treatment, including but not limited to, alleviating symptoms, eliminating the causation of the symptoms either on a temporary or permanent basis, or to preventing or slowing the appearance of symptoms and progression of the named disease, disorder or condition.

As described herein, the term 'patient' refers to a warm blooded animal such as a mammal which is afflicted with a particular disease, disorder or condition. It is explicitly understood that guinea pigs, dogs, cats, rats, mice, horses, cattle, sheep, and humans are examples of animals within the scope of the meaning of the term.

As used herein, 'disease' refers to an illness, sickness or an interruption, cessation or disorder of body functions, systems or organs.

As used herein, 'disorder' refers to a disturbance of function, structure or both resulting from a genetic or embryologic failure in development, or from exogenous factors such as poison, injury or disease.

As used herein, 'prophylaxis' refers to the prevention of disease.

As used herein, 'oncosis' or 'oncoses' refers to a condition characterized by the formation of one or more neoplasms or tumors.

As used herein, 'mycosis' or 'mycoses' refers to any disease that is caused by a fungus or yeast.

As used herein, 'pharmaceutical carrier' refers to known pharmaceutical excipients useful in formulating pharmaceutically active compounds for administration, and which are substantially nontoxic and nonsensitizing under conditions of use. The exact proportion of these excipients is determined by the solubility and chemical properties of the active compound, the chosen route of administration as well as standard pharmaceutical practice.

As used in the examples and preparations the terms used therein shall have the meanings indicated as follows: Me (methyl), Et (ethyl), Ph (phenyl), $Et_3N$ (triethylamine), DMF (dimethylformamide), DMSO (dimethylsulfoxide), TMS (tetramethylsilane), rt (room temperature), min or min. (minutes), h (hours), UV (ultraviolet), LC-MS (liquid chromatography mass spectrometry), t-Boc or Boc (tert-butoxycarbonyl), TFA (trifluoroacetic acid), HOAc (acetic acid), EtOAc (ethyl acetate), g (gram), mg (milligram), μg (microgram), ng (nanogram), mL (milliter), μL (microliter), L (liter); HPLC (high-performance liquid chromatography), TLC (thin layer chromatography); rpm (revolutions per minute), g/L (grams per liter), l/min (liters per minute), mL/min (milliters per minute), M (molar), mM (millimolar), μM (micromolar), μCi (microCurie), CPM (counts per minute), rpm (revolutions per minute), mm (millimeter), μm (micrometer), μ (micron), nm (nanometer), ppm (parts per million), ° C. (degrees Celsius), and K (Kelvin).

The compounds according to the invention differ from substances known from the literature by their polarity, chemical structure, biological activity or by further physical properties.

The strain *Penicillium herquei* Bainer & Sartory, DSM 14142, forms, on glucose-, starch-, oat flake- or glycerol-containing nutrient solutions, the compound called penilenone (a subset of phenalenones) of the tautomeric formulae (II-A) and (II-B), which are designated below as compounds of the formula (II),

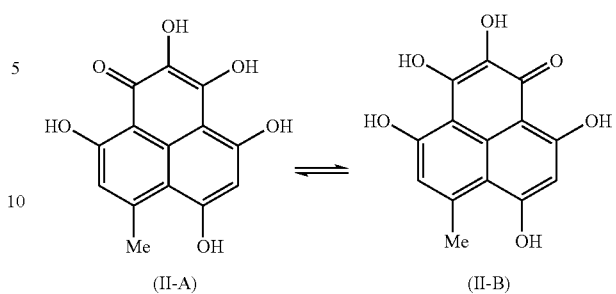

and atrovenetin of the tautomeric formulae (III-A) and (III-B), which are designated below as compounds of the formula (III). Atrovenetin and its known uses were removed from the claimed subject matter by means of a proviso.

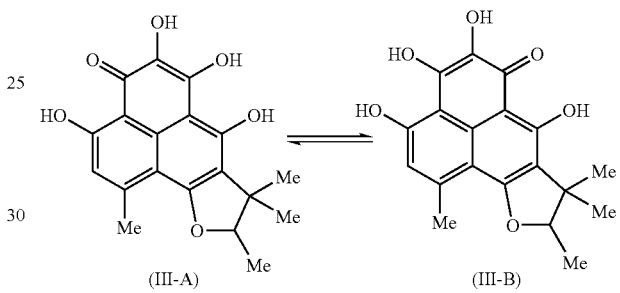

Compounds of the formulae (I-A) and (I-B), for which $R^1$ is not H, are isomeric forms, which are isolable separately from another, and which can be converted into one another, for example by removing the radical $R^1$, for which $R^1$ is equal to H, and subsequently, starting from the other tautomer in each case, derivatizing to give the other isomer of the compound of the formula (I-A) or (I-B) where $R^1$ is not H. The compounds of the formulae (I-A) and (I-B) are designated below by way of summary as the compound of the formula (I).

The compounds of the formulae (II-A) and (II-B) are tautomers and cannot be isolated from one another separately under customary conditions (e.g. room temperature). Compounds of the formulae (II-A) and (II-B) are designated below by way of summary as the compound of the formula (II).

The compounds of the formulae (III-A) and (III-B) are likewise tautomers and cannot be isolated from one another separately under customary conditions (e.g. room temperature). Compounds of the formulae (III-A) and (III-B) are designated below by way of summary as the compound of the formula (III).

Compounds of the formulae (I-A) and (I-B), for which $R^1$ is equal to H, can be selectively derivatized according to the present invention by reacting the hydroxyl groups with alkylating agents in a manner well known to one skilled in the art, such as is described, for example, by Jerry March in the book Advanced Organic Chemistry, John Wiley & Sons, 4th Edition, 1992. Alkylating agents are, for example, diazomethane derivatives, preferably trimethylsilyldiazomethane. In order to carry out derivatization reactions selectively, it may be advantageous before the reaction to introduce suitable protective groups in a manner well known to one skilled in the art. The protective groups are removed after the derivatization reaction and the product is then purified.

Until now, no selective alkylation of phenalenones to give the compounds according to the invention has been described. For example, the reaction of desoxyherqueinone with diazomethane leads, according to Suga et al. (Bull. Chem Soc. Jpn., 56, 3661-3666, 1983), to the desoxyherqueinone dimethyl ether or to the isomeric compound ent-atrovenetin trimethyl ether.

Compounds of the formulae (I-A) and (I-B), for which $R^1$ is equal to H, can be prepared, for example, by ether cleavage of compounds of the formulae (I-A) and (I-B), for which $R^1$ is not H. Ether cleavages can be carried out by methods well known to one skilled in the art, such as is described, for example, by Jerry March in the book Advanced Organic Chemistry, John Wiley & Sons, 4th Edition, 1992.

The invention therefore further relates to a compound of the formula (I), which has the formula (II), or to a pharmaceutically acceptable salt of the compound of formula (II).

The invention therefore furthermore relates to a process for the preparation of a compound of formula (II), which comprises the steps of:
1. culturing the microorganism Penicillium herquei Bainer & Sartory, DSM 14142, or one of its variants or mutants in an aqueous nutrient medium,
2. isolating and purifying a compound of formula (II), and
3. optionally converting the compound of formula (II) into a pharmaceutically acceptable salt.

The invention further relates to a process for the preparation of a compound of formula (I), which comprises the steps of;
1. culturing the microorganism Penicillium herquei Bainer & Sartory, DSM 14142, or one of its variants or mutants in an aqueous nutrient medium,
2. a) isolating and purifying a compound of formula (II), or
   b) isolating and purifying the compound of formula (III),
3. a) derivatizing the compound of formula (II) to give a compound of formula (I), or
   b) derivatizing the compound of formula (III) to give a compound of formula (I), and
4. optionally converting the compound of formula (I) into a pharmaceutically acceptable salt.

The strain Penicillium herquei Bainer & Sartory, DSM 14142, forms, on glucose-, starch-, oat flake- or glycerol-containing nutrient solutions, penilenone and other secondary products.

An isolate of Penicillium herquei Bainer & Sartory was deposited at the Deutsche Sammlung von Mikroorganismen und Zellkulturen (German Collection of Microorganisms and Cell Cultures) GmbH (DSM), Mascheroder Weg 1B, 38124 Brunswick, Germany according to the rules of the Budapest Convention on Mar. 6, 2001 under the following number: DSM 14142.

The fungus Penicillium herquei Bainer & Sartory, DSM 14142, has a gray to luminous green substrate mycelium and very little aerial mycelium. Exudates are not formed on malt medium and dyes are not excreted into the medium. In culture, the strain forms the compact sporangia characteristic of Penicillium, 200-400×3.5-4.0 µm, which are rough on the surface. The "metulae" are relatively short, usually 10-12×3.0-5.0 µm and club-shaped. The phialida are arranged in 6-10 "verticilli", 7-10×3.0 µm, ampoule-shaped. The conidia are elliptical to "apiculate", 3.5-5.0×3.0-3.5 µm, having a smooth cell wall. The conidia are formed in parallel chains, up to 100 µm long.

Said process comprises the culturing of Penicillium herquei Bainer & Sartory, DSM 14142, its mutants and/or variants under aerobic conditions in a culture medium containing at least in each case one carbon and nitrogen source, inorganic salts and optionally trace elements.

The culturing is preferably carried out at a temperature between from about 20° to about 35° C. and at a pH between from about 2 to about 9.

Instead of the strain DSM 14142, its mutants and variants can also be employed, insofar as they produce the compounds according to the invention. Such mutants can be produced in a manner well known to one skilled in the art by physical means, for example irradiation, such as with ultraviolet or X-rays, or chemical mutagens, such as, for example, ethyl methanesulfonate (EMS); 2-hydroxy-4-methoxybenzophenone (MOB) or N-methyl-N'-nitro-N-nitrosoguanidine (MNNG).

Suitable preferred carbon sources for the fermentation are assimilable carbohydrates and sugar alcohols, such as glucose, lactose, sucrose or D-mannitol, and carbohydrate-containing natural products, such as, for example, malt extract or yeast extract. Suitable nitrogen-containing nutrients are amino acids, peptides and proteins, and their degradation products, such as casein, peptones or tryptones, furthermore meat extracts, yeast extracts, ground seeds, for example corn, wheat, beans, soy, rice or cotton, distillation residues of alcohol production, meat meals or yeast extracts, and also ammonium salts and nitrates, but in particular also synthetically or biosynthetically obtained peptides. Inorganic salts which the nutrient solution can contain are, for example, chlorides, carbonates, sulfates or phosphates of the alkali metals or alkaline earth metals, iron, zinc, cobalt and manganese. Trace elements which the nutrient solution can contain are, for example, molybdenum, copper, nickel or selenium.

The formation of the compounds according to the invention proceeds particularly well, for example, in a nutrient solution which contains from about 0.05% to about 5%, preferably from about 1% to about 2%, of malt extract, from about 0.05% to about 3%, preferably from about 0.05% to about 1%, of yeast extract and from about 0.2% to about 5%, preferably from about 0.5% to about 2%, of glucose, from about 0.5% to about 3%, preferably from about 1.5% to about 3%, of oat flakes. The % concentration is in each case based on the weight of the entire nutrient solution.

In this nutrient solution, Penicillium herquei Bainer & Sartory, DSM 14142, forms a mixture of the compounds according to the invention. Depending on the composition of the nutrient solution, the quantitative amount of one or more of the compounds according to the invention can vary. Moreover, the synthesis of individual compounds can be controlled by the media composition, so that a compound is not produced at all or is produced in an amount below the detection limit of the assay method.

The culturing of the microorganism is carried out aerobically, that is, for example, submersed with shaking or stirring in shaker flasks or fermenters or on solid medium, optionally with introduction of air or oxygen. Culturing can be carried out over a temperature range from about 15° C.

to about 30° C., preferably from about 20° C. to about 30° C., in particular from about 25° C. to about 30° C. The pH range should be between from about 4 to about 10, preferably between from about 6.5 to about 7.5. The microorganism is in general cultured under these conditions over a period from about 48 hours to about 720 hours, preferably from about 72 hours to about 350 hours. The culturing is advantageously carried out in a number of stages, i.e., one or more precultures are first prepared in a liquid nutrient medium, which is then inoculated into the actual production medium, the main culture, for example in the volume ratio from about 1:10 to about 1:100. The preculture is obtained, for example, by inoculating the mycelium into a nutrient solution and allowing it to grow from about 20 hours to about 120 hours, preferably from about 48 hours to about 72 hours. The mycelium can be obtained, for example, by allowing the strain to grow from about 1 day to 42 days, preferably from about 21 days to 35 days, on a solid or liquid nutrient medium, for example yeast malt agar, oat flake agar or potato dextrose agar.

The course of fermentation and the screening for mutants and variants which produce the compounds according to the invention can be monitored according to methods well known to one skilled in the art, such as, for example, by testing the biological activity in bioassays or by chromatographic methods such as thin-layer chromatography (TLC) or high-performance liquid chromatography (HPLC).

The fungus *Penicillium herquei* Bainer & Sartory, DSM 14142, can form the compounds according to the invention by means of a surface or stand culture on solid nutrient media. Solid nutrient media are prepared by addition of, for example, agar or gelatin to aqueous nutrient media. It is moreover possible to obtain the compounds according to the invention by fermentation of the fungus *Penicillium herquei* Bainer & Sartory, DSM 14142, in the submersed process, i.e., in aqueous suspension. The compounds according to the invention can occur both in the mycelium and in the culture filtrate, usually the main amount is found in the cell mass. It is therefore expedient to separate the fermentation solution by filtration or centrifugation. The filtrate is extracted using an adsorption resin as a solid phase. The mycelium, and also the surface culture, is efficiently extracted with an organic solvent, for example methanol or propan-2-ol.

The extraction can be carried out over a wide pH range, but it is expedient to work in a neutral or weakly acidic medium, preferably between from about pH 3 to about pH 7. The extracts can be concentrated and dried, for example, in vacuo.

The compounds of formula (II) and of formula (III) are substances, which are unstable if suitable measures are not taken during the isolation and purification process. It has been found that the penilenones can be obtained in very good yields from cultures of the strain DSM 14142 if 1) work is carried out under reducing conditions during the isolation and purification process, e.g. always in the presence of ascorbic acid; 2) the isolation is carried out in acidic medium at a pH of less than 7, preferably in the pH range from about pH 2 to about pH 5; 3) during the purification step only mild agents are used, such as, for example, adsorption resins as chromatographic supports; and 4) the presence of amines is excluded during the entire process.

A suitable method for the isolation of the compounds according to the invention is partitioning in a manner well known to one skilled in the art. Another method of purification is chromatography on adsorption resins such as, for example, on Diaion® HP-20 (Mitsubishi Casei Corp., Tokyo), on Amberlite® XAD 7 (Rohm and Haas, USA), on Amberchrom® CG, (Toso Haas, Philadelphia, USA) or on the like. Also suitable under the circumstances indicated are numerous reverse-phase supports, e.g. $RP_8$ and $RP_{18}$, such as have generally become known, for example, in the context of high-pressure liquid chromatography (HPLC). A further purification possibility under the circumstances indicated is the use of "normal-phase" chromatographic supports, such as, for example, silica gel or $Al_2O_3$ or others in a manner well known to one skilled in the art. An alternative isolation process is the use of molecular sieves, such as, for example, Fractogel® TSK HW-40, Sephadex® G-25 and others, in a manner well known to one skilled in the art.

It is moreover possible to obtain the compounds of the formula (I) according to the invention after enrichment by crystallization, where, for example, organic solvents and their mixtures, either anhydrous or with addition of water, can be used.

An additional process for the isolation and purification of the compounds according to the invention consists in the use of anion exchangers, preferably in the pH range from about pH 4 to about pH 7, and cation exchangers, preferably in the pH range from about pH 2 to about pH 5. Particularly suitable for this is the use of buffer solutions to which portions of organic solvents have been added.

However, it is also possible to isolate and/or to purify the compounds according to the invention by sublimation.

A particularly advantageous purification method for the isolation of the compounds according to the invention is crystallization, which is carried out in a manner well known to one skilled in the art.

The compounds of the formula (I) according to the invention can be converted into the corresponding pharmaceutically acceptable salts according to methods well known to one skilled in the art. Pharmaceutically acceptable salts of the compounds according to the invention are understood as meaning both inorganic and organic salts, such as are described in Remingtons Pharmaceutical Sciences (17th edition, page 1418 [1985]). Possible salts are in particular alkali metal salts, ammonium salts, alkaline earth metal salts, salts with pharmaceutically acceptable amines and salts with inorganic or organic acids such as, for example, HCl, HBr, $H_2SO_4$, maleic acid, fumaric acid. Possible salts, however, are also complexes with metal ions, such as, for example, with calcium, magnesium, zinc, iron or others. The compounds of the formula (I) have a marked tendency to bind ions, preferably cations, in complex form.

It has surprisingly been found that since the compounds of formula (I) according to the invention have strong cytostatic effects, they are therefore suitable for the therapy and/or prophylaxis of diseases which are caused by uncontrolled growth of tissue or cells, or oncoses. It is particularly worthy of note that the compounds according to the invention have no cross-resistance at all with conventional cytostatics.

It has been found that the compounds of the formula (I) inhibit protein kinases. The kinases belong to the transferases, which transfer phosphate radicals from adenosine triphosphate to other substrates. Proteins and enzymes are phosphorylated and modified in their activity by the protein kinases, usually on serine, threonine or tyrosine side chains, which has been recognized as a widespread regulation principle in metabolism and signal transduction. In cancer, the diseased tissue proliferates in an uncontrolled manner and an intervention into the regulation of the kinase-controlled proliferation is therefore desirable. A number of kinases are involved in the cascade of cell proliferation. Several of these kinases are inhibited by the compounds according to the invention.

Moreover to be emphasized is an antimicrobial inhibitory action of the compounds of formula (I) according to the invention on bacteria, such as, for example, *Staphylococcus aureus, Streptomyces murinus* and against fungi, such as *Aspergillus niger*, which can cause stubborn, life-threatening infectious diseases. The antimicrobial activity can be demonstrated, for example, by "agar diffusion tests" as are well known to one skilled in the art, such as, for example the test "antibiogram on solid nutrient plates with antibiotic diffusion" as described by J. Müller and H. Melchinger, "Methoden der Mikrobiologie", Franck'sche Verlagsgesellschaft, 189-192 (1964). Thus, penilenone on an agar plate containing *Streptomyces murinus* culture in a solution of 1 mg per mL causes an inhibition halo of 11 mm and in a solution of 0.1 mg per mL an inhibition halo of 8 mm. The compounds of the formula (I) according to the invention are therefore likewise suitable for the treatment and/or prophylaxis of bacterial infections and/or fungal diseases (micosis or mycoses).

The compounds of the formula (I) can also be used as antioxidants. Antioxidants (oxidation inhibitors) are organic compounds which inhibit or prevent undesired changes in the substances to be protected caused by the effects of oxygen. Antioxidants are needed, for example, in plastics for protection against ageing, in fats for protection against rancidity, in oils against resinification, in aromatic substances against odor impairment, in foodstuffs, and in pharmaceuticals. The action of the antioxidants usually consists in acting as radical scavengers for the free radicals occurring in the oxidation. The antioxidative action of atrovenetin (compound of the formula (III)) has already been described by Y. Ishikawa et al. (J. Am. Oil Chem. Soc. 68, 666-668, 1991). Microbial antioxidants, however, are often too weak or not highly tolerable in their action. There is therefore a great need for novel, efficacious and tolerable antioxidants. The compounds of the formula (I) are highly active antioxidants, which considerably exceed atrovenetin in its antioxidant action. While atrovenetin in solution and in solid form reacts only slowly with atmospheric oxygen (for example in hours), penilenone of the formula (II), for example, combines with oxygen within seconds or in a few minutes. This increased affinity of penilenone for oxygen, however, is decidedly advantageous for very oxidation-sensitive substances.

Another chemical peculiarity of the compounds according to the invention is the ability for complex formation with polyvalent, preferably di- and tri-valent, cations such as, for example, with $Ca^{2+}$, $Mg^{2+}$, $Zn^{2+}$, or $Fe^{3+}$. The complex formation ability can be advantageous for the production of pharmaceuticals, thus, for example, inhibitors of matrix metalloproteases (MMPs) have become known which are able to bind the zinc of these enzymes. However, other possibilities of use are also conceivable in diseases whose expression is manifested in an abnormal metal ion concentration in the body. It is also possible to make the complex formation ability of the compounds according to the invention utilizable outside medicine, for example in water technology, in bodycare compositions, and in polymerization technology [Ullmans Enzyklopädie der Technischen Chemie (Ullman's Encyclopedia of Industrial Chemistry), 5th edition, A 10, 95-100, 1985-1995].

The compounds of formula (I) according to the invention can likewise act in the treatment of rheumatic diseases, for example rheumatoid arthritis. The active principle in the reduction of oxidative stress in rheumatoid arthritis by free radical scavengers or antioxidants has been described, for example, by Ostrakhovitch and Afanas (Biochemical Pharmacology, 2001, 743-746).

The present invention accordingly also relates to the use of the compounds of formula (I) according to the invention as pharmaceutical compositions, in particular for the treatment and/or prophylaxis of oncoses, bacterial infections, mycoses, rheumatic diseases and diseases which can be treated by the inhibition of matrix metalloproteases.

In addition, the present invention relates to a pharmaceutical composition containing at least one of the compounds according to the invention.

Said pharmaceutical composition is produced by mixing at least one compound of formula (I) with one or more pharmaceutically acceptable excipients and the mixture is formed into a suitable form for administration.

The pharmaceutical compositions according to the invention can be administered enterally (orally), parenterally (intramuscularly or intravenously), rectally or locally (topically). They can be administered in the form of solutions, powders, tablets, capsules including microcapsules, ointments, creams, gels or suppositories. Possible pharmaceutically acceptable excipients for formulations of this type are the pharmaceutically acceptable liquid or solid fillers and extenders, solvents, emulsifiers, lubricants, flavoring agents, colorants and/or buffer substances. As a suitable dose, from about 0.1 mg/kg to about 1000 mg/kg, preferably from about 0.2 mg/kg to about 100 mg/kg of body weight are administered. They are suitably administered in dose units which contain at least the efficacious daily amount of the compounds according to the invention, e.g. from about 30 mg to about 3000 mg, preferably from about 50 mg to about 1000 mg.

EXPERIMENTAL

The following examples are intended to serve to illustrate the invention in greater detail, and are not intended to restrict the breadth of the invention in any manner.

EXAMPLE 1

Preparation of a Glycerol Culture of *Penicillium herquei* Bainer & Sartory, DSM 14142

Innoculate 30 mL of nutrient solution (malt extract 2.0%, yeast extract 0.2%, glucose 1.0%, $(NH_4)_2HPO_4$ 0.05%, pH 6.0) in a sterile 100 mL Erlenmeyer flask with the strain *Penicillium herquei* Bainer & Sartory, DSM 14142, and incubate on a rotating shaker for 6 days at 25° C. and 140 rpm. A 1.5 mL sample of this culture is then diluted with 2.5 mL of 80% glycerol and stored at −135° C.

EXAMPLE 2

Preparation of a Preculture in an Erlenmeyer Flask of *Penicillium herquei* Bainer & Sartory, DSM 14142

Innoculate 100 mL of nutrient solution (malt extract 2.0%, yeast extract 0.2%, glucose 1.0%, $(NH_4)_2HPO_4$ 0.05%, pH 6.0) in a sterile 300 mL Erlenmeyer flask with the strain *Penicillium herquei* Bainer & Sartory, DSM 14142, and incubate on a rotating shaker for 4 days at 25° C. and 140 rpm. A 2 mL sample of this preculture is then utilized as innoculum for the preparation of the main cultures.

EXAMPLE 3

Preparation of a Main Culture of *Penicillium herquei* Bainer & Sartory, DSM 14142

A sterile 300 mL Erlenmeyer flask containing 100 mL of nutrient solution (malt extract 2.0%, yeast extract 0.2%, glucose 1.0%, $(NH_4)_2HPO_4$ 0.05%, pH 6) is inoculated with a culture grown in a slant tube (same nutrient solution, but with 2% agar) or with 2 mL of a preculture (see example 2) and incubated at 140 rpm and 25° C. on a shaker. The maximum production of one or more penilenone compounds according to the invention is achieved after about 144 hours. For inoculation of 10 L to 200 L fermenters, a 96 hour- to 144 hour-old submersed culture (inoculation amount about 10%) of the same nutrient solution suffices. The conditions for this fermenter are:
  Temperature 25° C.
  Stirrer speed: 200 rpm
  Aeration 15 L/min Foam formation can be suppressed by repeated addition of ethanolic polyol solution. The production maximum is achieved after from about 96 hours to about 144 hours.

EXAMPLE 4

Isolation of Compounds (II) and (III)

Five liters of culture solution, obtained according to example 3, were centrifuged and the cell mass (0.5 liter) was extracted with 2 liters of methanol, to which 0.1% ascorbic acid has been added. The clear-filtered methanolic phase was concentrated to 1 L in vacuo and applied to a column of 1 liter capacity, packed with adsorption resin MCI Gel® CHP20P. Column dimensions: width×height: 7 cm×27 cm. Elution was carried out using a solvent gradient of 10% propan-2-ol to 90% propan-2-ol in 0.1% aqueous ascorbic acid solution. The column effluent (140 mL/minute) was collected in fractions of 250 ml each. The penilenone-containing fractions 23 to 26 (mixture of the compounds of the formulae (II-A) and (II-B), in summary called compounds of the formula (II)) and the atrovenetin-containing fractions 43 to 51 (mixture of the compounds of the formulae (III-A) and (III-B), in summary called compounds of the formula (III)), which were checked by HPLC analyses, were collected and concentrated in vacuo. The combined fractions were in each case concentrated in vacuo and stored cold. Penilenone (260 mg of the compound of formula (II) crystallized from fractions 23 to 26, while fractions 43 to 51 afforded 1.2 g of atrovenetin (the compound of formula (III)). In each instance, the crystalline material was filtered off under an argon protective gas atmosphere and stored cold with exclusion of oxygen.

EXAMPLE 5

Isolation and Purification by HPLC

| | |
|---|---|
| Column: | Superspher 100 RP-18e ®, 250-4, with precolumn, |
| Mobile phase: | 2 minutes: 5% acetonitrile in 0.1% phosphoric acid, |
| | 18 minutes: gradient of 5% to 100% acetonitrile in 0.1% phosphoric acid, then |
| | 100% acetonitrile constant. |
| Flow rate: | 1 mL per minute, |
| | Detection by UV absorption at 210 nm. |

A retention time of 13.5 minutes was found for the compound of formula (II), and 20.5 minutes for the compound of formula (III).

EXAMPLE 6

Characterization of the Compound of Formula (II)

The physicochemical and spectroscopic properties of penilenone can be summarized as follows:

Appearance:
  Yellow crystalline substance, soluble in medium polar and polar organic solvents, not very soluble in water. The melting point is not determinable because of decomposition. Stable in mildly acidic medium under reducing conditions. Under the influence of oxygen, penilenone turns green in neutral medium or in the presence of amines.

| | |
|---|---|
| Empirical formula: | $C_{14}H_{10}O_6$ |
| Molecular weight: | 274.23 |

By means of ESI+ mass spectrometry, a molecular ion 275.2 $[M+H]^+$ was found, and under ESI (negative) conditions 273 $[M-H]^-$ or 271 $[M-3H]^-$ was measured.

UV maxima: 215 nm, 248 (sh) nm, 275 (sh) nm, 389 nm.

TABLE 1

NMR data - $^1H$ and $^{13}C$ chemical shifts δ (in ppm) of penilenone of formula (II) in DMSO-$d_6$ (TMS) at 300K (numbering for the purpose of the NMR analysis does not correspond to the IUPAC nomenclature).

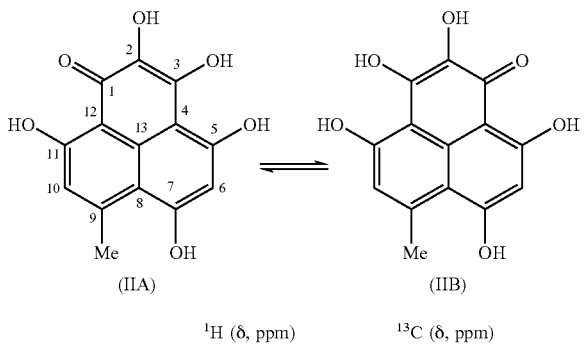

(IIA)　　　　　　　(IIB)

| | $^1H$ (δ, ppm) | $^{13}C$ (δ, ppm) |
|---|---|---|
| 1 | — | a) |
| 2 | — | 131.12 |
| 3 | — | a) |
| 4 | — | 102.22 |
| 5 | — | ~170.2 (broad) |
| 6 | 6.44 | 99.72 |
| 7 | — | 165.89 |
| 7-OH | 11.63 | — |
| 8 | — | 110.71 |
| 9 | — | 145.42 |
| 9-Me | 2.81 | 25.13 |
| 10 | 6.81 | 116.48 |
| 11 | — | ~163.0 (broad) |
| 12 | — | 105.04 |
| 13 | — | 124.86 | a)For C3 and C5, no signal is observed in the $^{13}C$ spectrum.

EXAMPLE 7

Preparation of Penilenone Dimethylether Derivatives of Formulae (IV-A) and (IV-B)

A solution of 40 mg of the compound of formula (II) (penilenone, isolated according to Example 4) in 30 mL of tetrahydrofuran was treated with 0.5 mL of 2.0 M (trimethylsilyl)diazomethane in hexane [Aldrich, cat. no. 36,283-2]. After one hour, the reaction was ended by addition of water and the solvent was distilled off in vacuo. The reaction product is then separated on a Nucleosil HD® column (21 mm×250 mm). The eluent used was a gradient of 10% to 99% acetonitrile in 0.1% acetic acid. The column flow, 20 mL per minute, was collected in fractions. The fractions which contained the methylation products were in each case combined, concentrated in vacuo and crystallized.

Penilenone dimethyl ether (6 mg) of formula (IV-A), empirical formula: $C_{16}H_{14}O_6$, molecular weight: 302.29, and 1 mg of penilenone dimethyl ether of formula (IV-B), empirical formula: $C_{16}H_{14}O_6$, molecular weight: 302.29, were obtained.

Properties of penilenone dimethyl ether of formula (IV-A):

UV maxima: 216 nm, 242 nm, 280 nm (sh), 387 nm.

TABLE 2

NMR data - $^1$H- and $^{13}$C-chemical shifts δ (in ppm) of penilenone dimethyl ether of formula (IV-A) in DMSO-$d_6$ (TMS) at 300K (numbering for the purpose of the NMR analysis does not correspond to the IUPAC nomenclature).

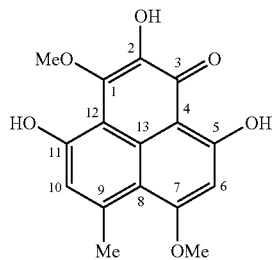

(IV-A)

| | $^1$H (δ, ppm) | $^{13}$C (δ, ppm) |
|---|---|---|
| 1 | — | 148.25 |
| 1-OMe | 4.14 | 60.97 |
| 2 | — | 137.12 |
| 2-OH | ~9.3 (broad) | — |
| 3 | — | 174.13[a] |
| 4 | — | 104.79 |
| 5 | — | 174.28[a] |
| 5-OH | 17.29 | — |
| 6 | 6.57 | 96.82 |
| 7 | — | 168.03 |
| 7-OMe | 4.04 | 56.45 |
| 8 | — | 111.30 |
| 9 | — | 143.18 |
| 9-Me | 2.74 | 25.12 |
| 10 | 6.88 | 117.65 |
| 11 | — | 159.10 |
| 11-OH | ~10.5 (broad) | — |
| 12 | — | 105.72 |
| 13 | — | 124.58 |

[a] C3 and C5 cannot be clearly differentiated.

Properties of penilenone dimethyl ether of formula (IV-B):

UV maxima: 213 nm, 241 nm and 390 nm.

TABLE 3

NMR data - $^1$H and $^{13}$C chemical shifts δ (in ppm) of penilenone dimethyl ether of formula (IV-B) in DMSO-$d_6$ (TMS) at 300K (numbering for the purpose of the NMR analysis does not correspond to the IUPAC nomenclature).

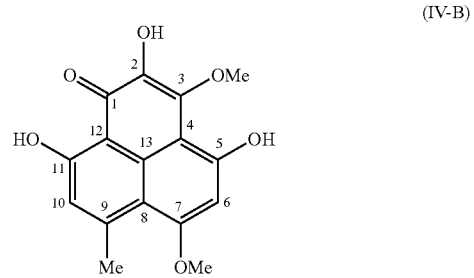

(IV-B)

| | $^1$H (δ, ppm) | $^{13}$C (δ, ppm) |
|---|---|---|
| 1 | — | 176.16 |
| 2 | — | 136.10 |
| 2-OH | broad | — |
| 3 | — | 149.54 |
| 3-OMe | 4.18 | 61.07 |
| 4 | — | 101.12 |
| 5 | — | 162.49 |
| 5-OH | broad | — |
| 6 | 6.66 | 97.44 |
| 7 | — | 163.72 |
| 7-OMe | 4.00 | 56.17 |
| 8 | — | 110.63 |
| 9 | — | 149.31 |
| 9-Me | 2.78 | 25.86 |
| 10 | 6.87 | 117.65 |
| 11 | — | 169.56 |
| 11-OH | 16.74 | — |
| 12 | — | 108.22 |
| 13 | — | 124.51 |

EXAMPLE 8

Preparation of Atrovenetin Monomethyl Ether Derivatives (V-A) and (V-B)

A solution of 100 mg of the compound of formula (III) (atrovenetin, prepared according to example 4) and 5 mL of tetrahydrofuran was treated with 1 mL of 2.0 M (trimethylsilyl)diazomethane in hexane [Aldrich, cat. no. 36,283-2]. After 15 minutes, the reaction was ended by addition of water and the solvent was distilled off in vacuo. The reaction product is then separated on a Nucleosil AB® column (21 mm×250 mm). The eluent used was a gradient of 10% to 99% acetonitrile in 0.02% trifluoroacetic acid, which has been adjusted to pH 4.5 with ammonium hydroxide. The column flow, 15 ml per minute, was collected in fractions. The fractions which contained the methylation products were in each case combined, concentrated in vacuo and crystallized.

Atrovenetin monomethyl ether (V-A) (24 mg), empirical formula: $C_{20}H_{20}O_6$, molecular weight: 356.38, and atrovenetin monomethyl ether (V-B) (10 mg), empirical formula $C_{20}H_{20}O_6$, molecular weight: 356.38 were obtained.

Propeties of atrovenetin monomethyl ether (V-A):

UV maxima: 218 nm, 260 nm (sh), 394 nm.

TABLE 4

NMR data - $^1$H and $^{13}$C chemical shifts δ (in ppm) of atrovenetin monomethyl ether (V-A) in DMSO-$d_6$ (TMS) at 300K (numbering for the purpose of the NMR analysis does not correspond to the IUPAC nomenclature).

(V-A)

[Structure of V-A]

| | $^1$H (δ, ppm) | $^{13}$C (δ, ppm) |
|---|---|---|
| 1 | — | 147.64 |
| 1-OMe | 4.16 | 60.94 |
| 2 | — | 137.35 |
| 2-OH | 9.26 | — |
| 3 | — | 174.04 |
| 4 | — | 105.81 |
| 5 | — | 170.14 |
| 5-OH | 17.45 | — |
| 6 | — | 117.94 |
| 7 | — | 166.28 |
| 8 | — | 107.35 |
| 9 | — | 142.91 |
| 9-Me | 2.76 | 22.90 |
| 10 | 6.91 | 116.71 |
| 11 | — | 159.95 |
| 11-OH | 10.63 | — |
| 12 | — | 105.63 |
| 13 | — | 124.10 |
| 14 | 4.75 | 91.03 |
| 14-Me | 1.46 | 14.39 |
| 15 | — | 42.57 |
| 15-Me | 1.51 | 25.31 |
| 15-Me' | 1.27 | 20.42 |

Properties at atrovenetin monomethyl ether (V-B):

UV maxima: 222 nm, 282 nm, 385 nm.

TABLE 5

NMR data - $^1$H and $^{13}$C chemical shifts δ (in ppm) of atrovenetin monomethyl ether (V-B) in DMSO-$d_6$ at 300K (numbering for the purpose of the NMR analysis does not correspond to the IUPAC nomenclature).

(V-B)

[Structure of V-B]

| | $^1$H (δ, ppm) | $^{13}$C (δ, ppm) |
|---|---|---|
| 1 | — | 173.97 |
| 2 | — | 135.31 |

TABLE 5-continued

NMR data - $^1$H and $^{13}$C chemical shifts δ (in ppm) of atrovenetin monomethyl ether (V-B) in DMSO-$d_6$ at 300K (numbering for the purpose of the NMR analysis does not correspond to the IUPAC nomenclature).

(V-B)

[Structure of V-B]

| | $^1$H (δ, ppm) | $^{13}$C (δ, ppm) |
|---|---|---|
| 2-OH | 9.21 | — |
| 3 | — | 149.90 |
| 3-OMe | 4.27 | 61.50 |
| 4 | — | 101.74 |
| 5 | — | 158.77 |
| 5-OH | 10.63 | — |
| 6 | — | 118.96 |
| 7 | — | 162.55 |
| 8 | — | 106.20 |
| 9 | — | 149.30 |
| 9-Me | 2.78 | 23.69 |
| 10 | 6.88 | 117.21 |
| 11 | — | 171.98 |
| 11-OH | 17.18 | — |
| 12 | — | 108.14 |
| 13 | — | 123.22 |
| 14 | 4.68 | 90.41 |
| 14-Me | 1.45 | 14.25 |
| 15 | — | 43.21 |
| 15-Me | 1.51 | 25.13 |
| 15-Me | 1.26 | 20.42 |

What is claimed is:

1. A compound of formula (I-A) or of formula (I-B),

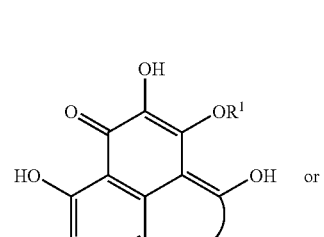

(I-A)

or

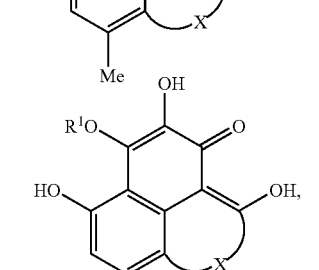

(I-B)

wherein:

X is a group of formula (I-C) or of formula (I-D),

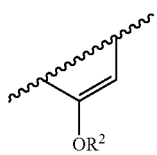 (I-C)

or

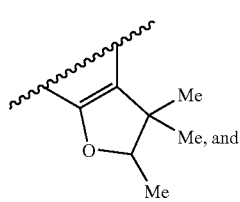 (I-D)

wherein:

R¹ and, if present, R² simultaneously are H, $C_1$-$C_6$-alkyl, $C_2$-$C_6$-alkenyl or $C_2$-$C_6$-alkynyl, wherein said $C_1$-$C_6$-alkyl, $C_2$-$C_6$-alkenyl or $C_2$-$C_6$-alkynyl substituents are optionally mono- or disubstituted by —OH, =O, —O—$C_1$-$C_6$-alkyl, —O—$C_2$-$C_6$-alkenyl, —$C_6$-$C_{10}$-aryl, —NH—$C_1$-$C_6$-alkyl, —NH—$C_2$-$C_6$-alkenyl, —$NH_2$, or halogen, wherein said —O—$C_1$—$C_6$—alkyl, —O—$C_2$—$C_6$—alkenyl, —$C_6$—$C_{10}$—aryl, —NH—$C_1$—$C_6$—alkyl, and —NH—$C_2$—$C_2$—$C_6$—alkenyl substituents are optionally substituted by —CN, —NH—C(O)—($C_1$—$C_6$—alkyl) or =NOH, or a stereoisomeric form of the compound of formula (I-A) or (I-B), or mixtures of the stereoisomeric forms thereof in any ratio, or a pharmaceutically acceptable salt thereof, and with the proviso that when R¹ is H, X is the group of formula (I-C) and with the proviso that both R¹ and R² are not simultaneously H.

2. The compound of formul (I-A) or (I-B) according to claim 1 wherein R¹ and R² are H or $C_1$-$C_6$-alkyl and with the proviso that both R¹ and R² are not simultaneously H.

3. The compound according to claim 2 which is the compound of formula (IV-A),

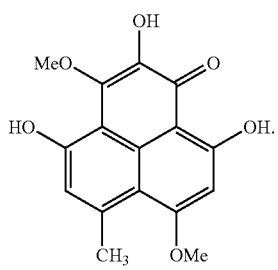 (IV-A)

4. The compound according to claim 2 which is the compound of formula (IV-B,

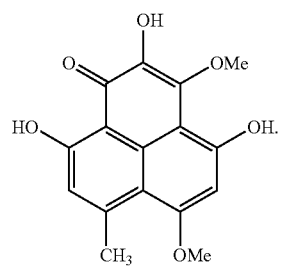 (IV-B)

5. The compound according to claim 2 which is the compound of formula (V-A),

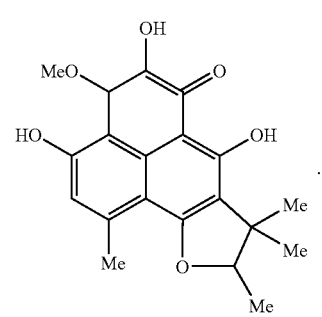 (V-A)

6. The compound according to claim 2 which is the compound of formula (V-B),

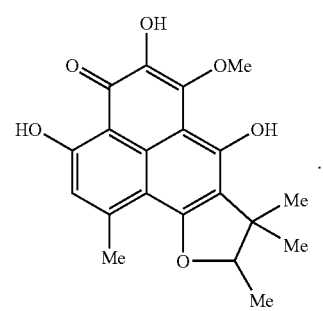 (V-B)

7. A process for the preparation of the compound of formula (I-A) or (I-B) according to claim 1 comprising the steps of:
a) culturing the microorganism *Penicillium herquei* Bainer & Sartory, DSM 14142, in an aqueous nutrient medium,
b) isolating and purifying a compound of formula (II-A) or (II-B),

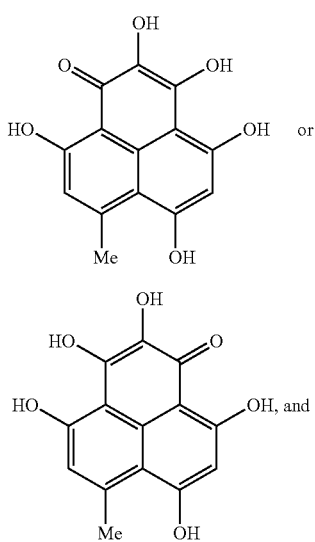

(II-A)

(II-B)

c) derivatizing the compound of formula (II-A) or (II-B) to give the compound of formula (I-A) or (I-B) wherein X is a group of formula (I-C), or
d) isolating and purifying a compound of formula (III-A) or (III-B),

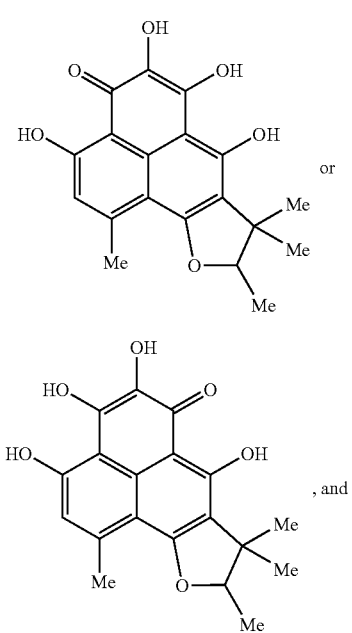

(III-A)

(III-B)

e) derivatizing the compound of formula (III-A) or (III-B) to give the compound of formula (I-A) or (I-B) wherein X is a group of formula (I-D), and
f) optionally converting the compound of formula (I-A) or (I-B) from step c or step e into a pharmaceutically acceptable salt.

8. The process according to claim 7 wherein the derivatizing is accomplished by means of an alkylating agent.

9. The process according to claim 8 wherein the alkylating agent is a diazomethane derivative.

10. An antioxidant composition comprising a compound as set forth in claim 1.

11. A method for the treatment or prophylaxis of bacterial infections comprising administering to a patient in need of said treatment or prophylaxis an antibacterially effective amount of a compound of formula (I-A) or of formula (I-B),

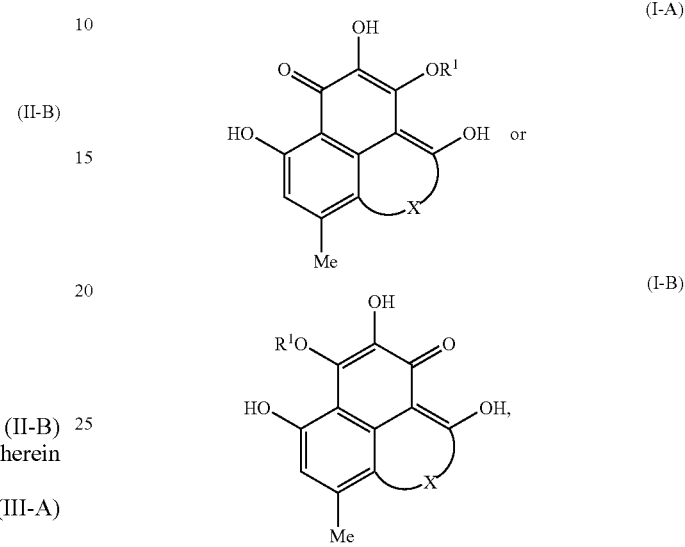

(I-A)

(I-B)

wherein:
X is a group of formula (I-C) or of formula (I-D),

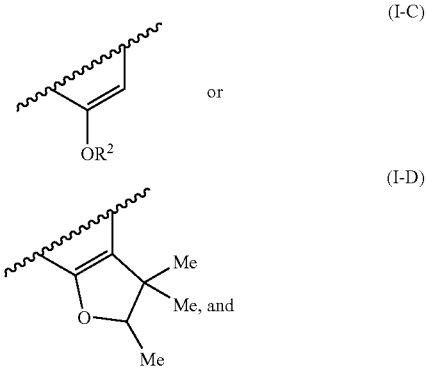

(I-C)

(I-D)

wherein:
R$_1$ and, if present, R$_2$ simultaneously are H, C$_1$-C$_6$-alkyl, C$_2$-C$_6$-alkenyl or C$_2$-C$_6$-alkynyl, wherein said C$_1$-C$_6$-alkyl, C$_2$-C$_6$-alkenyl or C$_2$-C$_6$-alkynyl substituents are optionally mono- or disubstituted by —OH, =O, —O—C$_1$-C$_6$-alkyl, —O-C$_2$-C$_6$-alkenyl, —C$_6$-C$_{10}$-aryl, —NH—C$_1$-C$_6$-alkyl, —NH—C$_2$-C$_6$-alkenyl, —NH$_2$, or halogen, wherein said —O—C$_1$-C$_6$-alkyl, —O—C$_2$-C$_6$-alkenyl, —C$_6$-C$_{10}$-aryl, —NH—C$_1$-C$_6$-alkyl, and —NH—C$_2$-C$_6$-alkenyl substituents are optionally substituted by —CN, —NH—C(O)—(C$_1$-C$_6$-alkyl) or =NOH, or a stereoisomeric form of the compound of formula (I-A) or (I-B), or mixtures of the stereoisomeric forms thereof in any ratio, or a pharmaceutically acceptable salt thereof, and
with the proviso that when $R^1$ is H, X is the group of formula (I-C).

12. A method for the treatment or prophylaxis of mycoses comprising administering to a patient in need of said treatment or prophylaxis an antimycotically effective amount of a compound of formula (I-A) or of formula (I-B),

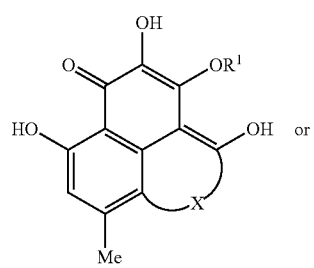

(I-A)

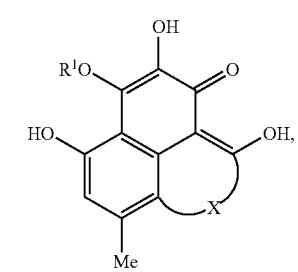

(I-B)

wherein:
X is a group of formula (I-C) or of formula (I-D),

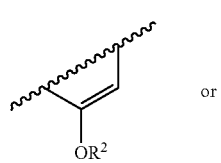

(I-C)

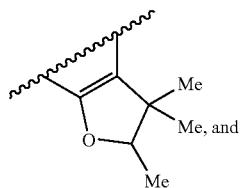

(I-D)

wherein:
$R^1$ and, if present, $R^2$ simultaneously are H, $C_1$-$C_6$-alkyl, $C_2$-$C_6$-alkenyl or $C_2$-$C_6$-alkynyl, wherein said $C_1$-$C_6$-alkyl, $C_2$-$C_6$-alkenyl or $C_2$-$C_6$-alkynyl substituents are optionally mono- or disubstituted by —OH, =O, —O—$C_1$-$C_6$-alkyl, —O—$C_2$-$C_6$-alkenyl, —$C_6$-$C_{10}$-aryl, —NH—$C_1$-$C_6$-alkyl, —NH—$C_2$-$C_6$-alkenyl, —$NH_2$, or halogen,
wherein said —O—$C_1$-$C_6$-alkyl, —O—$C_2$-$C_6$-alkenyl, —$C_6$-$C_{10}$-aryl, —NH—$C_1$-$C_6$-alkyl, and —NH—$C_2$-$C_6$-alkenyl substituents are optionally substituted by —CN, —NH—C(O)—($C_1$-$C_6$-alkyl) or =NOH, or a stereoisomeric form of the compound of formula (I-A) or (I-B), or mixtures of the stereoisomeric forms thereof in any ratio, or
a pharmaceutically acceptable salt thereof, and
with the proviso that when $R^1$ is H, X is the group of formula (I-C).

13. A pharmaceutical composition comprising a pharmaceutically acceptable carrier and an effective amount of the compound of formula (I-A) or of formula (I-B),

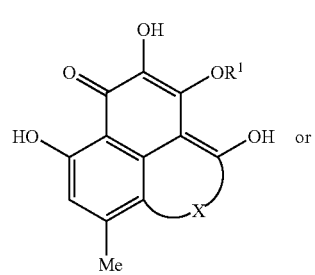

(I-A)

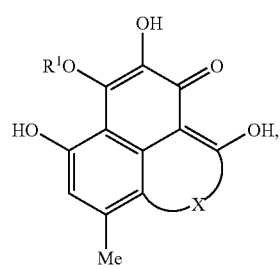

(I-B)

wherein:
X is a group of formula (I-C) or of formula (I-D),

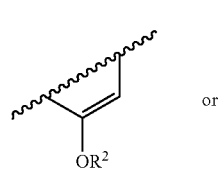

(I-C)

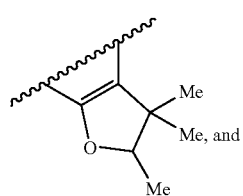

(I-D)

wherein:
$R^1$ and, if present, $R^2$ simultaneously are H, $C_1$-$C_6$-alkyl, $C_2$-$C_6$-alkenyl or $C_2$-$C_6$-alkynyl, wherein said $C_1$-$C_6$-alkyl, $C_2$-$C_6$-alkenyl or $C_2$-$C_6$-alkynyl substituents are optionally mono- or disubstituted by –OH, =O, —O—$C_1$-$C_6$-alkyl, —O—$C_2$-$C_6$-alkenyl, —$C_6$-$C_{10}$-aryl, —NH-$C_1$-$C_6$-alkyl, —NH—$C_2$-$C_6$-alkenyl, —$NH_2$, or halogen,
wherein said —O—$C_1$-$C_6$-alkyl, —O—$C_2$-$C_6$-alkenyl, —$C_6$-$C_{10}$-aryl, —NH—$C_1$-$C_6$-alkyl, and —NH—$C_2$-$C_6$-alkenyl substituents are optionally substituted by —CN, —NH—C(O)—($C_1$-$C_6$-alkyl) or =NOH, or a stereoisomeric form of the compound of formula (I-A) or (I-B), or mixtures of the stereoisomeric forms thereof in any ratio, or a pharmaceutically acceptable salt thereof, and with the proviso that when $R^1$ is H, X is the group of formula (I-C).

14. A compound isolated from the strain, *Penicillium herquei* Bainer & Sartory, DSM 14142, said compound having the formula (II-A) or (II-B):

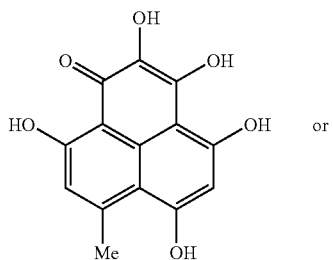
(II-A)

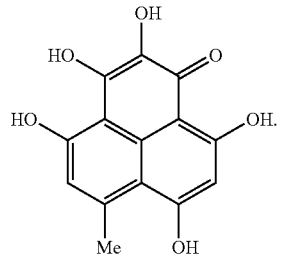
(II-B)

15. A process for the preparation of the compound of formula (II-A) or (II-B) according to claim 14 comprising the steps of:
a) culturing the microorganism *Penicillium herquei* Bainer & Sartory, DSM 14142, in an aqueous nutrient medium,
b) isolating and purifying the compound of formula (II-A) or (II-B), and
c) optionally converting the compound of formula (II-A) or (II-B) into a pharmaceutically acceptable salt.

* * * * *